United States Patent [19]

Kesling, Jr.

[11] 4,281,173
[45] Jul. 28, 1981

[54] PREPARATION OF UNSATURATED DIESTERS BY CATALYTIC OXIDATIVE CARBONYLATION OF DIOLEFINS

[75] Inventor: Haven S. Kesling, Jr., Drexel Hill, Pa.

[73] Assignee: Atlantic Richfield Company, Los Angeles, Calif.

[21] Appl. No.: 99,377

[22] Filed: Dec. 3, 1979

[51] Int. Cl.$^3$ ............................................. C07C 67/38
[52] U.S. Cl. ....................................... 560/204; 560/97
[58] Field of Search ................. 560/204, 97, 192, 193, 560/81

[56] References Cited

U.S. PATENT DOCUMENTS

| | | | |
|---|---|---|---|
| 4,039,572 | 8/1972 | Funakoshi et al. | 560/204 |
| 4,171,450 | 10/1979 | Kesling et al. | 560/204 |

*Primary Examiner*—Natalie Trousof
*Assistant Examiner*—Vera C. Clarke
*Attorney, Agent, or Firm*—Delbert E. McCaslin

[57] ABSTRACT

A process for the preparation of an unsaturated diester having the formula

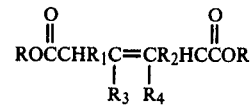

wherein R is alkyl having 1 to 8 carbon atoms or aralkyl having 6 carbon atoms in the ring and from 1 to 4 carbon atoms in the alkyl moiety, and $R_1$, $R_2$, $R_3$ and $R_4$ are the same or different and are each hydrogen, halogen, alkyl having 1 to 4 carbon atoms or aryl having 6 carbon atoms in the ring, by reacting carbon monoxide and oxygen with a diolefin having the formula

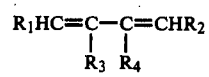

wherein $R_1$, $R_2$, $R_3$ and $R_4$ are as aforesaid, in the presence of a catalytic amount of a platinum group metal compound, a copper or iron oxidant salt compound, a soluble vanadium salt and a stoichiometric amount of a dehydrating agent. Optionally, an anhydrous-halogen containing acid may be included.

Alternatively, a ligand or coordination complex compound of the metal salt compound, and catalytic quantities of an alcohol may be employed.

10 Claims, No Drawings

PREPARATION OF UNSATURATED DIESTERS BY CATALYTIC OXIDATIVE CARBONYLATION OF DIOLEFINS

BACKGROUND OF THE INVENTION

It is known in the art to prepare an unsaturated diester by the catalytic oxidative carbonylation of a diolefin. More particularly, it is known to synthesize diesters by reacting carbon monoxide, oxygen and a diolefin such as 1,3-butadiene, isoprene, chloroprene, 2,3-dimethylbutadiene, 1,3-pentadiene and the like, under elevated temperature and pressure conditions in the presence of a catalytic amount of a ruthenium, rhodium, palladium, osmium, iridium or platinum metal salt compound of mixtures thereof, a copper (I), copper (II), iron (II) or iron (III) oxidant salt compound and a stoichiometric amount of a dehydrating agent which may be, for example, an orthoester, ketal, acetal, or trialkyl orthoborate. Co-catalytic ligands or coordination complex compounds of the metal salt compounds and catalytic quantities of a primary, secondary or tertiary saturated alcohol, while not required in this prior art process, may also be employed.

In the aforesaid process, the oxycarbonylation catalyst markedly deactivates after but two uses. The reason for deactivation is now thought to be the formation of dimethyl oxalate as a non-selective product in the oxycarbonylation reaction. Hydrolysis of the dimethyl oxalate by water formed during the reoxidation of copper (I) to copper (II) or iron (II) to iron (III) forms oxalic acid. Oxalic acid complexes with the soluble copper (II) or iron (III) reoxidant resulting in the formation of insoluble and inactive copper (II) or iron (III) oxalate. It is felt that because of copper (II) or iron (III) losses associated with the formation of copper (II) or iron (III) oxalate, the reoxidation of the platinum group metal such as palladium (O) by copper (II) or iron (III), is incomplete or slow resulting in agglomeration of the platinum group metal as well as a general loss in catalyst activity.

SUMMARY OF THE INVENTION

Unexpectedly in accordance with the present invention, it has been discovered that the presence of a catalytic amount of a soluble vanadium salt such as vanadium (III) chloride prevents premature catalyst deactivation. It is felt that said vanadium salt causes the in situ oxidative destruction of oxalic acid before the formation of copper (II) or iron (III) oxalate can occur.

Although, in accordance with the present invention, the catalyst system remains active after multiple catalyst recycles, it has been observed that final product selectivity drops rapidly after but two cycles. Unexpectedly, it has been found that the addition of an effective amount of an anhydrous halogen-containing acid such as hydrochloric acid, prevents final product selectivity losses during multiple catalyst recycles. In lieu of direct addition of anhydrous halogen-containing acid, it may be formed in situ by the addition of a halogen-containing acid donor such as 1-chloro-1-methoxycyclohexane which undergoes equilibrium thermal dissociation in the oxycarbonylation reaction to afford hydrochloric acid and 1-methoxycyclohexene.

In summary, the present invention is an improvement on the above discussed prior art process in that the addition of an effective amount of a vanadium salt which is soluble in the reaction mixture under reaction conditions maintains catalyst activity on multiple recycle and the addition of an anhydrous halogen-containing acid maintains final product selectivity during multiple recycles of the catalyst.

DESCRIPTION OF THE INVENTION

In accordance with this invention, an unsaturated diester having the formula

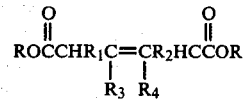

wherein R and $R_1$ to $R_4$ are as hereinafter described, is produced by reacting, under liquid phase conditions, a mixture of carbon monoxide and oxygen or an oxygen-containing gas with a diolefin, at elevated temperatures and pressures in the presence of a catalyst system comprising (1) a platinum group metal or platinum group metal compound or mixtures thereof, with or without a ligand or coordination complex compound such as lithium chloride; (2) a catalytic amount of a copper (I), copper (II), iron (II) or iron (III) metal oxidant salt compound and (3) a vanadium salt which is soluble in the reaction mixture under reaction conditions. In addition, a stoichiometric quantity of a suitable dehydrating agent, based on the diolefin being reacted, is employed in the reaction in order to reduce the problems associated with the presence of water in the system which is produced therein by the oxidant-reoxidation reaction. Optionally, the reaction may also be carried out in the presence of an anhydrous halogen-containing acid. While not essential to the oxidative carbonylation of the diolefin as set forth herein, a catalytic amount of an alcohol especially an aliphatic alcohol, is preferably employed in the reaction to aid in initiating the oxidative carbonylation reaction. The reactants are initially charged in an essentially anhydrous condition.

A general postulated equation for the reaction of the present invention may for example be represented as follows:

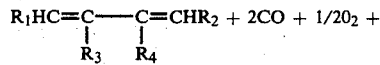

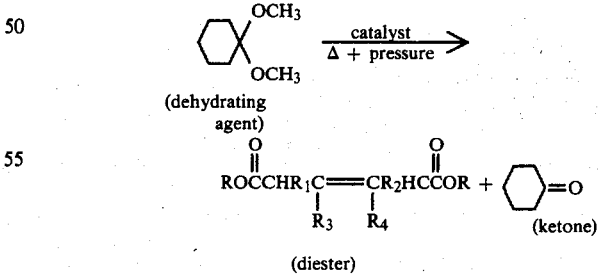

wherein R is alkyl having 1 to 4 carbon atoms or aralkyl having 6 carbon atoms in the ring and 1 to 4 carbon atoms in the alkyl moiety and $R_1$, $R_2$, $R_3$ and $R_4$ are the same or different and are each hydrogen, halogen, alkyl having 1 to 4 carbon atoms or aryl having 6 carbon atoms in the ring.

The reaction between the diolefin, carbon monoxide, oxygen, and dehydrating agent may be carried out in an autoclave or any other appropriate reactor. Although the order of addition of reactants and catalyst components may vary, a general procedure is to charge the diolefin, dehydrating agent, platinum group metal compound, oxidant salt compound and the soluble vanadium salt and, optionally, the anhydrous halogen-containing acid into the reaction vessel, and if desired a ligand or coordination complex compound and a catalytic quantity of an alcohol, then introduce the proper amount of carbon monoxide and oxygen to the desired reaction pressure and then heat the mixture to the desired temperature for the appropriate period. The reaction can be carried out batchwise or as a continuous process and the order of addition of reactants and catalyst may be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, liquid-liquid solvent extraction, etc., to effect separation of the diesters from unreacted materials, platinum group metal salt compound, oxidant salt compound, soluble vanadium salt and/or anhydrous halogen-containing acid by products, including for example, when reacting 1,3-butadiene, dimethylhex-2, 4-diendioate, methylpent-3-enoate, methylpent-2,4-dienoate, methyl-3-methoxypent-4-enoate, methyl-5-methoxypent-3-enoate, dimethyl oxalate and $CO_2$, etc. Catalysts, including solvents which may be employed, may be recycled to the system.

The diolefins which may be employed in concentrations of from about 10 to 80 weight percent, preferably 20 to 60 weight percent, or on a mole per mole basis with the dehydrating agent employed, and suitable for use in the process of the present invention conform to the general formula

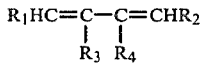

wherein $R_1$ to $R_4$, which may be the same or different, is hydrogen, halogen, alkyl having 1 to 4 carbon atoms or aryl having 6 carbon atoms in the ring. Representative diolefins within the above noted formula include for example, butadiene, isoprene, chloroprene, 2,3-dimethyl-, 2,3-diethyl-, 2,3-dipropyl- and 2,3-dibutyl-butadiene, 1,3- and 2,4-heptadienes, 1,3-pentadiene, piperylene, 2-ethyl-1,3-butadiene, 1-phenylbutadiene, 1,4-diphenylbutadiene, 2-chloro-3-methylbutadiene, 1-chlorobutadiene, 2,5-dimethyl-2,4-hexadiene, 2-bromobutadiene, 2-iodobutadiene, 2-chloro-1-phenylbutadiene, etc. Butadiene and isoprene are the preferred diolefins and butadiene is most preferred.

Suitable dehydrating agents which may be employed and in at least stoichiometric amounts in the process of the invention include for example acetals, ketals, carboxylic ortho esters, trialkylorthoborates and dialkoxycycloalkanes.

The acetals and ketals suitable for use in the process of the present invention conform to the general formulae:

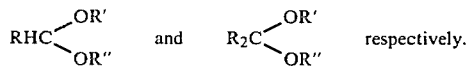

R may be substituted or unsubstituted alkyl having 1 to 20 carbon atoms, preferably 1 to 10 carbon atoms. R may also be substituted or unsubstituted alicyclic, or aryl having one or more benzenoid rings, preferably not more than 3 rings, which may be fused or joined by single valency bonds. R' and R" which may be the same or different may be substituted or unsubstituted alkyl having 1 to 8 carbon atoms, preferably 1 to 4 carbon atoms, in the alkyl chain or aralkyl having 6 carbon atoms in the ring and from 1 to 4 carbon atoms in the alkyl moiety. R, R' and R" may contain substituents such as amido, alkoxy, amino, carboxy, cyano, etc. Representative acetals suitable for use in this invention include, for example, the 1,1-dialkoxyalkanes such as dimethoxymethane, dibutoxymethane, 1,1-dimethoxyethane 1,1-dimethoxypropane, ethyl diethoxyacetate, 1,1,2-trimethoxyethane, 1,1-dimethoxy-2-propene, and dimethoxy- and diethoxy-phenylmethane, etc. In a like manner for example the acetals 1-methoxy-, 1-ethoxy- and 1-propoxytetrahydrofuran, 2,5-diethoxytetrahydrofuran, and 2-ethoxy-4-methyl-3,4-dihydro-2H-pyran etc. may be employed. Representative ketals suitable for use in this invention include for example, 2,2-dimethoxy-, 2,2-diethoxy- and 2,2-dipropoxy-propane, butane, pentane, etc., 3,3-dimethoxy- and 3,3-diethoxy-1-pentene, 1-butene, etc., 1,1-dimethoxycyclohexane, 1,1-diethoxycyclohexane, 1,1-dibutoxycyclohexane, etc., 1,1-dibutoxy-4-methylcyclohexane, 1,1-dimethoxy-1,2,3,4-tetrahydronaphthalene, etc. and 1,1-bis(2l-propenoxy)cyclohexane.

The carboxylic ortho esters suitable for use in the process of the invention conform to the general formula

wherein R may be hydrogen or substituted or unsubstituted alkyl having 1 to 20 carbon atoms, preferably 1 to 10 carbon atoms. R may also be alicyclic, or aryl containing one or more benzenoid rings, preferably not more than 3 rings, which may be fused or joined by single valency bonds. R', R" and R'" which may be the same or different may be substituted or unsubstituted alkyl having 1 to 8 carbon atoms preferably 1 to 4 carbon atoms in the alkyl chain or aralkyl having 6 carbon atoms in the ring and from 1 to 4 carbon atoms in the alkyl moiety. R, R', R" and R'" may contain substituents such as amido, alkoxy, amino, carboxy, cyano, etc. Representative carboxylic ortho esters suitable for use in this invention include, for example trimethyl orthoformate, triethyl orthoformate, triphenyl orthoformate, tri-n-propyl orthoformate, etc., triethyl, tripropyl, tributyl, trimethyl orthoacetate, etc., trimethyl, triethyl, tripropyl, tributylorthopropionate, etc., trimethyl, triethyl, tripropyl, tributyl orthobutyrate, etc., trimethyl, triethyl, tripropyl, tributyl, orthoisobutyrate, etc., trimethyl, triethyl, tripropyl, tributyl orthocyanoacetate, etc., trimethyl, triethyl, tripropyl, tributyl orthophenylacetate, etc., trimethyl, triethyl, tripropyl, tributyl ortho-α-chloroacetate, etc., trimethyl, triethyl, tripropyl, tributyl ortho-α-bromacetate, etc., trimethyl, triethyl, tripropyl, tributyl orthobenzoate, etc., trimethyl, triethyl, tripropyl, tributyl ortho-p-chlorobenzoate, etc., hexamethyl, p-diorthophthalate, etc., ethyl triethoxyacetate, hexaethyl orthooxalate, triethyl ortho-3-butynoate, etc. In a like manner the esters trimethyl, triethyl, tripropyl orthocarbonate, 2-isopropyl-2- methoxy-1,3-dioxolane, 2-methyl-2-ethoxy-1,3-dioxolane, 2,2-diethoxytetrahydrofuran, 2,2-diethoxychroman, 1,4,5-trioxaspiro[4,4]nonane, 2,6,7-trioxabicyclo[2,2,2]octanes, 2,4,20-trioxaadamantane-2,4,10-trioxatricyclo[3,3,1,1³,⁷] decane may be employed.

The orthoborate esters employed in at least stoichiometric quantities and suitable for use in the process of the present invention are preferably symmetrical and conform to the general formula

wherein R' is substituted or unsubstituted alkyl having 1 to 8 carbon atoms in the alkyl chain or aralkyl having 6 carbon atoms in the ring and from 1 to 4 carbon atoms in the alkyl moiety. Particularly preferred are the orthoborates wherein each R' is a straight chain alkyl group containing from 1 to 4 carbon atoms such as triethyl borate. Representative ortho borate esters suitable for use in this invention include, for example, trimethylborate, triethylborate, tri-2-chloroethyl borate, tritolyl borates, tri-methoxybenzyl borates, tri-chlorobenzyl borates, tri-benzyl borate, tri-4-butylphenyl borate, tri-n-propyl and tri-isopropyl borates, tri-(1,3-dichloro-2-propyl) borate, tri-n-butyl, tri-s-butyl and tri-t-butyl borates, tri (β,β,β-trichloro-t-butyl)borate, triphenyl borate, tri-o-chlorophenyl borate, tri-n-amyl borate, tri-t-amyl borate, tri-(o-phenylphenyl) borate, tri-n-hexyl borate, tri-3-heptyl borate, tri-3-pentyl borate, tri-n-octyl and tri-isooctyl borates, tri-(2-ethylhexyl)borate, tri-(methylisobutylcarbonyl) borate, tri(dissobutylcarbinyl) borate, tri-(2,5-dimethylbenzyl) borate, etc.

The dialkoxycycloalkanes, which are the preferred dehydrating agents for use in the present invention, in at least stoichiometric quantities, conform to the general formula

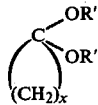

wherein R' is substituted or unsubstituted alkyl having 1 to 4 carbon atoms and x is an integer of from 4 to 9. R' may contain substitutents such as amido, alkoxy, amino, carboxy, cyano, etc. In addition, the cyclic ring may be substituted with alkyl having up to 4 carbon atoms. Dimethoxycyclohexane is the most preferred. Representative dialkoxycycloalkanes include for example, dimethoxy-, diethoxy-, dipropoxy- and dibutoxycyclopentanes, and corresponding dimethoxy, diethoxy, dipropoxy and dibutyoxycyclohexanes, heptanes, octanes, nonanes and decanes, as well as 4-ethyl-1,1-dimethoxycyclohexane, etc. A general postulated equation for the reaction using 1,1-dimethoxycyclohexane in the oxidative carbonylation of butadiene may be represented as follows:

CH₂=CH—CH=CH₂ + 2CO + 1/2O₂ +

(butadine)

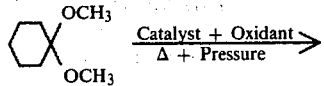

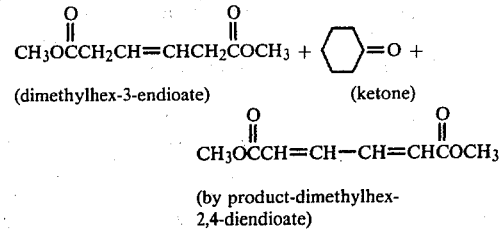

The platinum group metal compounds which may be employed in the process of this invention as catalyst are the palladium, platinum, rhodium, ruthenium, iridium, and osmium salts or mixtures thereof. Among the chemical forms of the platinum group metal salt compounds which can be used as such or as mixtures or formed in the reaction system from the metals per se are for example the palladium, platinum, rhodium, ruthenium, iridium and osmium, halides, sulfates, nitrates, oxides, oxalates, acetates and trifluroacetates, preferably the palladium (II) halides, particularly palladium (II) chloride. Representative catalytic platinum group metal salt compounds include, for example palladium (II) chloride, platinum (II) chloride, rhodium (III) chloride, ruthenium (III) chloride, palladium (II) sulfate, palladium (II) acetate, palladium (II) trifluroacetate, palladium (II) iodide, rhodium (III) bromide, iridium (III) chloride, platinum (II) sulfate, osmium (II) chloride, palladium (II) oxide, osmium tetroxide, iridium (III) sulfate, etc. As indicated above the metals as such may be added to the reaction as part of the catalyst mixture, the salt compound being formed in situ from at least a portion of the platinum group metal under reaction conditions.

The palladium, platinum, rhodium, ruthenium, osmium and iridium compounds employed may be in a homogeneous state in the reaction mixture at reaction conditions. Thus, the compounds may be present in solution, or suspension and may also be on support materials such as alumina, silica gel, aluminosilicates, activated carbon or zeolites or may be anchored to a polymer support. The compounds may be partially or completely soluble under reaction conditions. The reaction is generally carried out in the presence of a catalytic proportion of the platinum group metal salt compound and will proceed with small amounts of the metal salt compounds hereinabove described. Generally the proportions of the platinum group metal salt compound used in the reaction will be equivalent to between about 0.001 to 5 weight percent of the diolefin employed and are preferably employed in amounts between about 0.01 to 2 percent by weight of the diolefin employed. Larger or smaller amounts may be employed at varied pressures and temperatures.

As mentioned hereinabove, alternatively, a ligand or coordination complex compound of the platinum group metal salt compound may be employed in the process of the invention as co-catalyst in the catalytic mixture and thereby also achieve a pronounced increase in the selectivity for the unsaturated diester. The ligands may be for example, alkyl or aryl phosphines, arsines, or stibines or salts of the alkli metals, e.g., lithium, sodium, potassium, rubidium, cesium salts, such as lithium iodide, sodium chloride, potassium bromide, lithium acetate, lithium chloride, etc. The complexes of a metal salt compounds which are suitable for use in the process of the present invention include complex compounds of palladium, platinum, rhodium, ruthenium, osmium and iridium. The complex compounds may contain one or more atoms of the salt metals in the molecule and when more than one such atom is present, the metals may be the same or different. The mono- or polydentate ligands which are present in the molecule of the complex compounds and in which at least one of the electron-donating atoms is an atom of phosphorus, arsenic or antimony or a halide ion containing a lone pair of electrons may be, for example, organo-phosphines, -arsines and -stibines. Suitable monodentate ligands include alkyl phosphines such as trimethylphosphine and tributylphosphine, aryl-phosphines such as diethylphenylphosphine and radicals derived from such phosphines, for example the radical having the formula —$P(CH_3)_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is preferred to employ the alkali metal halides, particularly the lithium halides such as lithium chloride and lithium iodide.

Benzonitrile, acetonitrile, isocyanates, isothiocyanates, pyridine, pyridyls, pyrimidine, quinoline, isoquinoline may also serve as suitable ligands to modify the platinum group metal catalyst activity or catalyst solubility.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen, and halogen atoms; groups which may be bonded to the metal include, for example hydrocarbyl, hydrocarbyloxy, carbonyl, nitrosyl, cyano and $SnCl_3$—groups; molecules which may be bonded to the metal include, for example organic isocyanides and isothiocyanates. Examples of suitable complex compounds are those represented by the following formulae:

| | |
|---|---|
| $Na_2PdCl_4$ | $\pi$-allyl Paladium Complexes |
| $RhBr_3(PPhEt_2)_3$ | $Rh(CO)Cl(AsE_3)_2$ |
| $RhCl(CO)(PPhEt_2)_2$ | $RhCl(CO)(PEt_3)_2$ |
| $Rh(Ph_2PCH_2CH_2PPH_2)_2Cl$ | $PdCl_2(PPh_3)_2$ |
| $Rh[(PhO)_3P]_3Cl$ | $PdI_2(PPh_3)_2$ |
| $Li_2PdI_4$ | $PtCl_2(p\text{-}ClC_6H_4PBu_2)_2$ |
| | $(PhCN)_2PdCl_2$ |

The complex compounds employed may be introduced into the reaction mixture such as, or they may be formed in situ from a suitable platinum group metal or metal compound noted above and the desired ligand.

The ligand or complex compounds may be used in catalyst amounts of from 0 to 3 percent preferably from 0.1 to 1 percent by weight of a diolefin to be reacted although larger or smaller amounts may be employed at varied pressures or reaction rates.

The oxidant salt compounds which may be employed in an essentially anhydrous condition in the process of the present invention and in catalytic amounts of from 0.1 to 10 weight percent preferably 0.50 to 6 weight percent include the iron (II), iron (III), copper (I) and copper (II) salts such as the halides, sulfates, trifluoroacetates, nitrates, naphthanes, hex-3-endioates or acetates and preferably copper (II) chloride and iron (II) chloride. Representative oxidant salts include, for example, copper (II) sulfate, copper (II) trifluoroacetate, copper (II) acetate, copper (II) triflate, copper (II) fluorosulfonate, copper (I) chloride, copper (I) sulfate, iron (II) sulfate, iron (II) iodide, iron (II) chloride, iron (III) acetate, copper (II) hex-3-endioate, iron (II) hex-3-endioate and iron (III) trifluoroacetate.

The soluble vanadium salt which is employed in accordance with the present invention is preferably vanadium (III) chloride, bromide or iodide. The amount employed generally ranges from 0.3–3 weight percent.

The anhydrous halogen-containing acid which may be employed is preferably hydrochloric, hydrobromic or hydroiodic acid in a concentration of 0.01–1 mol/liter. Additionally and as noted hereinabove 1-chloro-1-chloro-1-methoxycyclohexane can be used as an in situ source of hydrochloric acid.

As indicated hereinabove, an alcohol in catalytic quantities may be employed in the process of the invention primarily to aid in initiating the oxidative carbonylation reaction. The alcohols may be employed in concentrations of from 0 to 75 and preferably 0.5 to 10 weight percent of the diolefin employed. The alcohols may be saturated monohydric primary, secondary or tertiary alcohols and conform to the general formula ROH, wherein R is an optionally substituted aliphatic or alicyclic group containing from 1 to 20 carbon atoms and preferably the unsubstituted aliphatic alcohols containing from 1 to 8 carbon atoms. R may also be substituted or unsubstituted aralkyl. In general, the substituents which may be amido, alkoxy, amino, carboxy, etc. radicals, in addition to the hydroxyl group, do not interfere with the reaction of the invention. Representative alcohols especially suitable for use in this invention are saturated monohydric alcohols such as methyl, ethyl, n-, iso-, sec-, and tert-butyl, amyl, hexyl, octyl, lauryl, n-, and isopropyl, cetyl, benzyl, chlorobenzyl and methoxybenzyl alcohols as well as, for example, tolylcarbinol, cyclohexanol, heptanols, decanols, undecanols, 2-ethyl hexanol, nonanol, myristyl alcohol, stearyl alcohol, methyl cyclohexanol, pentadecanol, oleyl and eicosonyl alcohols, and the like. The preferred alcohols are the primary and secondary monohyric saturated aliphatic alcohols, such as methanol, ethanol, 1- and 2-propanol, n-butyl alcohol, etc., up to 8 carbon atoms. The R group of the alcohol may be different from the R', R" or R''' of the dehydrating agents noted hereinabove resulting in the preparation of mixed diesters.

Solvents, if desired, which are chemically inert to the components of the reaction system may be employed, and in some cases, especially in the oxidative carbonylation of 1,3-butadiene, will improve the selectivity and conversion to the $C_6$-unsaturated diesters as well as the catalyst solubility or boiling point range for product and catalyst recovery. Suitable solvents include for example, dioxane, dimethylcarbonate, dimethyladipate, benzene, nitrobenzene, acetonitrile, tetrahydrofuran, methyl acetate, ethyl acetate, isopropyl acetate, n-propyl formate, butyl acetates, cyclohexyl acetate, n-propyl benzoate, lower alkyl phthalates, etc. the alkyl sulfones and sulfoxides such as propyl ethyl sulfoxide, diisopropyl sulfone, diisooctyl sulfoxide, acetone, cyclohexanone, methyl formate, etc.

The process of the present invention can be suitably performed by introducing the oxygen and carbon monoxide at a desired pressure into contact with the diolefin, dehydrating agent, the platinum group metal salt compound, the copper or iron oxidant salt and the soluble vanadium salt and, optionally, anhydrous halogen-containing acid and possibly a catalyic amount of an alcohol as well as co-catalytic amount of a ligand or coordination complex and heating to the desired temperature. In general, a carbon monoxide pressure of about 15 psig to about 5000 psig partial pressure and preferably about 500 psig to about 1800 psig is employed. Stoichiometric quantities of carbon monoxide are generally employed. However, an excess of carbon monoxide may be employed, for example, in continuous processes where a large excess of or high carbon monoxide requirements are generally utilized, a suitable recycle of the unreacted carbon monoxide may be employed. The reaction will proceed at temperatures of from about 25° C. to 200° C. It is generally preferred to operate the process at temperatures in the range of 80° C. to 150° C. to obtain a convenient rate of reaction with the particular diolefin. Lower temperatures may be employed but the reaction rate is slower. Higher temperatures may also be used depending of the diolefin to be reacted. At the higher temperatures the diolefin employed may be in the vapor state. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The reaction time is generally dependent upon the diolefin being reacted, temperature, pressure and on the amount and type of the catalyst, oxidant and dehydrating agent being charged as well as the type of equipment being employed. Reaction times will vary dependent on whether the process is continuous or batch and may vary from 10 to 600 minutes. Reaction time for butadiene is generally about 120 minutes.

The following examples are provided to illustrate the invention in accordance with the principles of this invention but are not to be construed as limiting the invention in any way except as indicated by the appended claims.

EXAMPLES 1-9

All reactants were charged into a 500 ml "Magnedrive" Hastelloy "C" autoclave. Reaction conditions included a reaction temperature of 100° C. at 1800 psi total system pressure. In all experiments, 1,3-butadiene (100 ml–1000 mmole) was allowed to come to thermal equilibrium before it was charged into the autoclave as a liquid via the use of a sight glass. Carbon monoxide (1100 psi) was charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 50 psi $O_2$ and 100 psi CO additions were made at intervals so that the gases were never potentially explosive. 144.00 g (1000 mmole) 1,1-dimethoxycyclohexane was used as a dehydration agent in each of the reactions along with 5.0 g (156 mmole) of methanol. The autoclave residence time for all of Examples 1–9 was 120 minutes and the oxygen addition frequency was 20 minutes. The stirring rate was 1000 rpm. The catalyst system comprised $PdCl_2$ (5.0 mmole), $CuCl_2$ (25 mmole) and LiCl (10.0 mmole) and additionally 10 mmole of LiCl was added to the 6th pass and an additional 25.0 mmole $CuCl_2$ was added to the 7th pass. Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 1 sets forth the results of Examples 1–9 which serve to illustrate the fact that the prior art 1,3-butadiene oxycarbonylation catalyst rapidly deactivates during the course of multiple recycle. Addition of fresh lithium chloride to the 6th pass failed to restore activity; however, addition of fresh copper (II) chloride to the 7th pass restored activity. Copper (II) oxalate was recovered and unequivocally identified by infrared analysis.

TABLE 1

| Example No. | 1 | 2 | 3 | 4 | 5 |
|---|---|---|---|---|---|
| Reaction Conditions | | | | | |
| Recycle Number | 1st Pass | 2nd Pass | 3rd Pass | 4th Pass | 5th Pass |
| Catalyst Concentration (moles/liter) | .002 | .0017 | .0016 | .0015 | .0015 |
| % Conversion | 33.3 | 28.6 | 18.3 | 12.7 | 10.1 |
| 1,1-Dimethoxycyclohexane Balance (%) | 96.9 | 103 | 101 | 98 | 97.9 |
| Butadiene Balance (%) | 97.4 | 95.1 | 90.5 | 99.4 | 94.8 |
| % of Original Activity | — | 85.9 | 55.0 | 38.1 | 30.3 |
| pH | 4.9 | 3.3 | 3.3 | 3.3 | 3.9 |
| Selectivity (mole %, based on BD) | | | | | |
| 1 = $CH_3O_2CCH=CHCH=CH_2$ | 3.3 | 1.2 | Trace | Trace | Trace |
| 2 = cisoid $CH_3OC(O)CH=CHCH=CH_2$ | Trace | Trace | Trace | Trace | Trace |
| 3 = transoid $CH_3OC(O)CH=CHCH=CH_2$ | 10.2 | 21.5 | 33.0 | 38.4 | 44.1 |
| 4 = $CH_3OC(O)CH_2CH(OCH_3)CH=CH_2$ | .6 | Trace | .3 | .3 | Trace |
| 6 = cis $CH_3OCH_2CH=CHCH_2CO_2CH_3$ | Trace | Trace | Trace | Trace | Trace |
| 7 = trans $CH_3OCH_2CH=CHCH_2CO_2CH_3$ | 1.5 | 1.4 | .4 | .7 | Trace |
| 12 = cis $CH_3O_2CCH_2CH=CHCH_2CO_2CH_3$ | 16.5 | 14.8 | 11.3 | 10.3 | 12.5 |
| 13 = trans $CH_3O_2CCH_2CH=CHCH_2CO_2CH_3$ | 68.0 | 61.4 | 55.0 | 50.3 | 43.5 |
| 12 & 13 (Total) | 84.5 | 76.2 | 66.3 | 60.6 | 56.0 |
| Selectivity (mole %, based on CO) | | | | | |
| 3 = transoid $CH_3OC(O)CH=CHCH=CH_2$ | 4.9 | 10.4 | 14.5 | 18.1 | 19.9 |
| 5 = $CH_3O(O)CC(O)CH_3$ | 3.5 | 9.6 | 21.1 | 14.6 | 18.4 |
| $CO_2$ | 7.3 | 5.2 | 8.7 | 9.5 | 10.9 |

TABLE 1-continued

| | | | | | |
|---|---|---|---|---|---|
| 12 & 13 (Total) | 81.8 | 73.7 | 55.5 | 57.2 | 50.7 |

| Example No. | 6 | 7 | 8 | 9 |
|---|---|---|---|---|
| Reaction Conditions | | | | |
| Recycle Number | 6th Pass | 7th Pass | 8th Pass | 9th Pass |
| Catalyst Concentration (moles/liter) | .0015 | .0015 | .0014 | .0014 |
| % Conversion | 7.6 | 18.4 | 15.3 | 15.7 |
| 1,1-Dimethoxycyclohexane Balance (%) | 100.2 | 102 | 98.9 | 95.7 |
| Butadiene Balance (%) | 92.3 | 87.5 | 84.8 | 85.3 |
| % of Original Activity | 22.8 | 55.3 | 46.0 | 47.2 |
| pH | 5.1 | 4.9 | 5.1 | 4.5 |
| Selectivity (mole %, based on BD) | | | | |
| 1 = $CH_3O_2CCH=CHCH=CH_2$ | Trace | 2.6 | Trace | Trace |
| 2 = cisoid $CH_3OC(O)CH=CHCH=CH_2$ | Trace | Trace | Trace | Trace |
| 3 = transoid $CH_3OC(O)CH=CHCH=CH_2$ | 57.2 | 26.8 | 38.2 | 37.0 |
| 4 = $CH_3OC(O)CH_2CH(OCH_3)CH=CH_2$ | Trace | 5.4 | .6 | Trace |
| 6 = cis $CH_3OCH_2CH=CHCH_2CO_2CH_3$ | Trace | Trace | Trace | Trace |
| 7 = trans $CH_3OCH_2CH=CHCH_2CO_2CH_3$ | Trace | 2.4 | .3 | Trace |
| 12 = cis $CH_3O_2CCH_2CH=CHCH_2CO_2CH_3$ | 9.2 | 13.8 | 12.4 | 12.7 |
| 13 = trans $CH_3O_2CCH_2CH=CHCH_2CO_2CH_3$ | 33.6 | 54.0 | 48.6 | 49.3 |
| 12 & 13 (Total) | 42.8 | 67.8 | 61.0 | 63.0 |
| Selectivity (mole %, based on CO) | | | | |
| 3 = transoid $CH_3OC(O)CH=CHCH=CH_2$ | 21.6 | 13.7 | 19.7 | 17.7 |
| 5 = $CH_3O(O)CC(O)OCH_3$ | 27.9 | 6.6 | 10.3 | 12.2 |
| $CO_2$ | 18.1 | 7.8 | 6.8 | 8.1 |
| 12 & 13 (Total) | 32.4 | 69.2 | 62.8 | 61.0 |

EXAMPLES 10-15

All reactants were charged into a 300 ml "Magnedrive" Hastelloy "C" autoclave. Reaction conditions included a reaction temperature of 100° C. at 1800 psi total system pressure. In all experiments, 1,3-butadiene (50 ml-500 mmole) was allowed to come to thermal equilibrium before it was charged into the autoclave as a liquid via the use of a sight glass. Carbon monoxide (1100 psi) and oxygen (75 psi) were charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 100 psi $O_2$ and 100 psi CO additions were made at intervals so that the gases were never potentially explosive. 72.00 g (500 mmole) 1,1-dimethoxycyclohexane was used as a dehydration agent in each of the reactions along with 2.5 (78 mmole) of methanol. The autoclave residence time for all of Examples 10-15 was 120 minutes and the oxygen addition frequency was 20 minutes. The stirring rate was 1500 rpm. The catalyst system comprised $PdCl_2$ (2.5 mmole), $CuCl_2$ (12.5 mmole), LiCl (5.0 mmole) and $VCl_3$ (2.5 mmoles). Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 2 sets forth the results of Examples 10-15 which serve to illustrate the effect of vanadium (III) chloride upon the course of multiple recycle of a palladium (II) chloride, copper (III) chloride and lithium chloride 1,3-butadiene oxycarbonolation catalyst.

TABLE 2

| Example No. | 10 | 11 | 12 | 13 | 14 | 15 |
|---|---|---|---|---|---|---|
| Reaction Conditions | | | | | | |
| Recycle Number | 1st Pass | 2nd Pass | 3rd Pass | 4th Pass | 5th Pass | 6th Pass |
| % Conversion | 34.9 | 33.4 | 34.6 | 29.7 | 25.3 | 31.2 |
| DMOC Balance (%) | 98.8 | 95.5 | 96.8 | 100.3 | 86.2 | 98.1 |
| Butadiene Balance (%) | 89.6 | 86.7 | 80.0 | 80.2 | 78.3 | 87.6 |
| % of Original Activity | — | 95.7 | 99.1 | 85.1 | 72.5 | 89.4 |
| pH | 4.9 | 4.9 | 5.1 | 5.1 | 5.1 | 5.1 |
| Selectivity (mole %, Based on BD) | | | | | | |
| 1 = $CH_3O_2CCH_2CH=CHCH_3$ | 7.8 | Trace | Trace | Trace | Trace | Trace |
| 2 = cisoid $CH_3OC(O)CH=CHCH=CH_2$ | Trace | Trace | Trace | Trace | Trace | Trace |
| 3 = transoid $CH_3OC(O)CH=CHCH=CH_2$ | 9.5 | 33.3 | 54.1 | 57.7 | 50.6 | 52.8 |
| 4 = $CH_3OC(O)CH_2CH(OCH_3)CH=CH_2$ | .8 | .1 | .3 | .5 | .5 | .3 |
| 6 = cis $CH_3OCH_2CH=CHCH_2CO_2CH_3$ | Trace | Trace | Trace | Trace | Trace | Trace |
| 7 = trans $CH_3OCH_2CH=CHCH_2CO_2CH_3$ | 2.8 | 1.8 | .8 | .7 | .6 | .5 |
| 12 = cis $CH_3O_2CCH_2CH=CHCH_2CO_2CH_3$ | 13.8 | 12.2 | 9.2 | 7.6 | 8.0 | 7.6 |
| 13 = trans $CH_3O_2CCH_2CH=CHCH_2CO_2CH_3$ | 59.8 | 47.7 | 32.5 | 29.0 | 33.2 | 33.6 |
| 14 = $CH_3O_2CCH=CHCH=CHCO_2CH_3$ | 2.9 | 4.9 | 3.1 | 4.7 | 7.3 | 5.3 |
| Total 12, 13, and 14 | 76.1 | 64.8 | 44.8 | 41.3 | 48.5 | 46.5 |
| Selectivity (mole %, Based on CO) | | | | | | |
| 1 = $CH_3O_2CCH_2CH=CHCH_3$ | 3.7 | Trace | Trace | Trace | Trace | Trace |
| 3 = transoid $CH_3OC(O)CH=CHCH=CH_2$ | 4.5 | 11.8 | 26.1 | 28.0 | 24.5 | 31.7 |
| 5 = $CH_3O(O)CC(O)CH_3$ | 3.0 | 9.8 | 12.3 | 14.7 | 11.6 | 3.2 |
| $CO_2=$ | 14.9 | 31.9 | 18.0 | 16.9 | 16.6 | 9.0 |

TABLE 2-continued

| Example No. | 10 | 11 | 12 | 13 | 14 | 15 |
|---|---|---|---|---|---|---|
| Total 12, 13 and 14 | 72.2 | 45.7 | 43.2 | 39.9 | 46.9 | 55.7 |

EXAMPLES 16-21

All reactants were charged into a 300 ml "Magnedrive" Hastelloy "C" autoclave. Reaction conditions included a reaction temperature of 100° C. at 1800 psi total system pressure. In all experiments, 1,3-butadiene (50 ml-500 mmole) was allowed to come to thermal equilibrium before it was charged into the autoclave as a liquid via the use of a sight glass. Carbon monoxide (1100 psi) was charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 50 psi $O_2$ and 100 psi CO additions were made at intervals so that the gases were never potentially explosive. 72.00 g (500 mmole) 1,1-dimethoxychlorohexane was used as a dehydration agent in each of the reactions along with 2.5 g (78 mmole) of methanol. The autoclave residence time for all of Examples 16-21 was 120 minutes and the oxygen addition frequency was 20 minutes. The stirring rate was 1000 rpm. The catalyst system comprised $PdCl_2$ (2.5 mmole), $CuCl_2$ (12.5 mmole), LiCl (5.0 mmole) and $VCl_3$ (5.0 mmole). Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 3 sets forth the results of Examples 16-21 which serve to illustrate the effect of the addition of small quantities of anhydrous hydrochloric acid to the catalyst system.

EXAMPLES 22-26

All reactants were charged into a 300 ml "Magnedrive" Hastelloy "C" autoclave. Reaction conditions included a reaction temperature of 100° C. at 1800 psi total system pressure. In all experiments, 1,3-butadiene (50 ml-500 mmole) was allowed to come to thermal equilibrium before it was charged into the autoclave as a liquid via the use of a sight glass. Carbon monoxide (1100 psi) was charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 50 psi $O_2$ and 100 psi CO additions were made at intervals so that the gases were never potentially explosive. 72.00 g (500 mmole) 1,1-dimethoxychlorohexane was used as a dehydration agent in each of the reactions along with 2.5 g (78 mmole) of methanol. The autoclave residence time for all of Examples 22-26 was 120 minutes and the oxygen addition frequency was 20 minutes. The stirring rate was 1000 rpm. The catalyst system comprised $Na_2PdCl_4$ (4.2 mmole), $CuCl_2$ (12.5 mmole), LiCl (5.0 mmole) and $VCl_3$ (5.0 mmole). Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 4 sets forth the results of Examples 22-26 which serve to illustrate the effect of the addition of anhydrous hydrochloric acid to the catalyst system.

TABLE 3

| Example No. | 16 | 17 | 18 | 19 | 20 | 21 |
|---|---|---|---|---|---|---|
| Recycle Number | 1st Pass | 2nd Pass | 3rd Pass | 4th Pass | 5th Pass | 6th Pass |
| Reaction Conditions | | | | | | |
| HCl (mmole) | — | 16.0 | 16.0 | 16.0 | 16.0 | 16.0 |
| $VCl_3$ (mmole) | 5.0 | — | — | — | — | — |
| % Conversion | 42.0 | 31.6 | 28.3 | 26.2 | 27.4 | 26.8 |
| DMOC Balance (%) | 91.2 | 79.6 | 82.6 | 95.3 | 95.5 | 96.2 |
| BD Balance (%) | 92.2 | 88.6 | 89.9 | 90.9 | 100 | 96.9 |
| % of Original Activity | — | 75.2 | 67.4 | 62.4 | 65.2 | 63.8 |
| Selectivity (mole %, based on BD) | | | | | | |
| 1 = $CH_3O_2CCH_2CH=CHCH_3$ | 2.7 | 1.0 | 3.0 | .2 | 2.3 | 2.2 |
| 2 = cisoid $CH_3OC(O)CH=CHCH=CH_2$ | trace | trace | trace | trace | trace | trace |
| 3 = transoid $CH_3OC(O)CH=CHCH=CH_2$ | 20.1 | 17.3 | 16.7 | 13.1 | 9.3 | 10.4 |
| 4 = $CH_3OC(O)CH_2CH(OCH_3)CH=CH_2$ | .5 | .7 | 1.6 | 1.4 | 1.0 | 1.1 |
| 6 = cis $CH_3OCH_2CH=CHCH_2CO_2CH_3$ | trace | trace | trace | trace | trace | trace |
| 7 = trans $CH_3OCH_2CH=CHCH_2CO_2CH_3$ | 4.1 | 3.5 | 3.3 | 2.9 | 2.3 | 2.2 |
| 12 = cis $CH_3O_2CCH_2CH=CHCH_2CO_2CH_3$ | 13.6 | 14.7 | 14.2 | 15.4 | 16.1 | 15.8 |
| 13 = trans $CH_3O_2CCH_2CH=CHCH_2CO_2CH_3$ | 56.2 | 60.1 | 58.3 | 65.0 | 68.3 | 67.0 |
| 14 = $CH_3OC(O)CH=CHCH—CHCO_2CH_3$ | 2.7 | 2.7 | 2.9 | 2.0 | .9 | 1.3 |
| Total 12, 13 and 14 | 72.5 | 77.5 | 75.4 | 82.4 | 85.3 | 84.1 |
| Selectivity (mole %, based on CO) | | | | | | |
| 1 = $CH_3O_2CCH_2CH=CHCH_3$ | 1.1 | .4 | 1.3 | .1 | 1.1 | 1.1 |
| 3 = transoid $CH_3OC(O)CH=CHCH=CH_2$ | 8.1 | 7.0 | 7.0 | 6.5 | 4.6 | 5.3 |
| 5 = $CH_3O(O)CC(O)OCH_3$ | 1.4 | 2.3 | 2.0 | .7 | .7 | 1.6 |
| $CO_2$ | 29.2 | 25.9 | 24.6 | 8.3 | 6.6 | 8.3 |
| Total 12, 13 and 14 | 58.4 | 62.7 | 63.1 | 82.3 | 85.3 | 81.6 |

TABLE 4

| Example No. | 22 | 23 | 24 | 25 | 26 |
|---|---|---|---|---|---|
| Recycle Number | 1st Pass | 2nd Pass | 3rd Pass | 4th Pass | 5th Pass |
| Reaction Conditions | | | | | |
| HCl (mmole) | — | — | 16.0 | 16.0 | 16.0 |
| $VCl_3$ (mmole) | — | 5.0 | — | — | — |
| % Conversion | 47.5 | 33.3 | 27.9 | 25.9 | 26.1 |
| DMOC Balance (%) | 98.3 | 78.3 | 86.6 | 94.5 | 95.6 |
| BD Balance (%) | 98.1 | 86.6 | 89.0 | 84.4 | 89.2 |
| % of Original Activity | — | — | 83.8 | 77.8 | 78.4 |
| Selectivity (mole %, based on BD) | | | | | |
| 1 = $CH_3O_2CCH_2CH=CHCH_3$ | trace | 9.1 | 3.3 | 5.5 | 4.9 |
| 2 = cisoid $CH_3OC(O)CH=CHCH=CH_2$ | trace | trace | trace | trace | trace |
| 3 = transoid $CH_3OC(O)CH=CHCH=CH_2$ | 9.7 | 6.7 | 8.8 | 7.9 | 8.3 |
| 4 = $CH_3OC(O)CH_2CH(OCH_3)CH=CH_2$ | trace | trace | .9 | 1.2 | .7 |
| 6 = cis $CH_3OCH_2CH=CHCH_2CO_2CH_3$ | trace | trace | trace | trace | trace |
| 7 = trans $CH_3OCH_2CH=CHCH_2CO_2CH_3$ | 4.6 | 4.0 | 2.8 | 2.2 | 2.1 |
| 12 = cis $CH_3O_2CCH_2CH=CHCH_2CO_2CH_3$ | 15.8 | 16.3 | 16.1 | 16.1 | 16.2 |
| 13 = trans $CH_3O_2CCH_2CH=CHCH_2CO_2CH_3$ | 66.0 | 62.3 | 65.5 | 64.7 | 65.5 |
| 14 = $CH_3OC(O)CH=CHCH=CHCO_2CH_3$ | 3.9 | 1.6 | 2.7 | 2.5 | 2.3 |
| Total 12, 13 and 14 | 85.7 | 80.2 | 84.3 | 83.3 | 84.0 |
| Selectivity (mole %, based on CO) | | | | | |
| 1 = $CH_3O_2CCH_2CH=CHCH_3$ | trace | 3.9 | 1.6 | 2.8 | 1.9 |
| 3 = transoid $CH_3OC(O)CH=CHCH=CH_2$ | 5.0 | 2.8 | 4.2 | 4.0 | 4.1 |
| 5 = $CH_3O(O)CC(O)OCH_3$ | .7 | 1.2 | 1.1 | 1.0 | 1.3 |
| $CO_2$ | 3.3 | 22.8 | 11.3 | 5.1 | 8.9 |
| Total 12, 13, and 14 | 88.7 | 67.5 | 80.1 | 85.2 | 83.8 |

EXAMPLES 27–38

All reactants were charged into a 300 ml "Magnedrive" Hastelloy "C" autoclave. Reaction conditions included a reaction temperature of 100° C. at 1800 psi total system pressure. In all experiments, 1,3-butadiene (50 ml-500 mmole) was allowed to come to thermal equilibrium before it was charged into the autoclave as a liquid via the use of a sight glass. Carbon monoxide (1100 psi) was charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 50 psi $O_2$ and 100 psi CO additions were made at intervals so that the gases were never potentially explosive. 72.00 g (500 mmole) 1,1-dimethoxychlorohexane was used as a dehydration agent in each of the reactions along with 2.5 g (78 mmole) of methanol. The autoclave residence time for all of Examples 27–38 was 120 minutes and the oxygen addition frequency was 20 minutes. The stirring rate was 1000 rpm. The catalyst system comprised $PdCl_2$ (2.5 mmole), $CuCl_2$ (12.5 mmole), LiCl (5.0 mmole) and $VCl_3$ (5.0 mmole). Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 5 sets forth the results of Examples 27–38 which serve to illustrate the effect of the addition of small quantities (varied concentrations) of anhydrous hydrochloric acid to the catalyst system.

TABLE 5

| Example No. | 27 | 28 | 29 | 30 | 31 | 32 |
|---|---|---|---|---|---|---|
| Recycle Number | 1st Pass | 2nd Pass | 3rd Pass | 4th Pass | 1st Pass | 2nd Pass |
| Reaction Conditions | | | | | | |
| HCL (mmole) | — | 16.0 | 16.0 | 16.0 | — | 8.0 |
| HCL (mole/liter) | — | .11 | .11 | .11 | — | .05 |
| $VCl_3$ (mmole) | 5.0 | — | — | — | 5.0 | — |
| % Conversion | 42.0 | 31.6 | 28.3 | 26.2 | 35.1 | 41.6 |
| DMOC Balance (%) | 91.2 | 79.6 | 82.6 | 95.3 | 97.6 | 98.4 |
| ED Balance (%) | 92.2 | 88.6 | 89.9 | 90.9 | 85.1 | 93.4 |
| % of Original Activity | — | 75.2 | 67.4 | 62.4 | — | 118.5 |
| Selectivity (mole %, on BD) | | | | | | |
| 1 = $CH_3O_2CCH_2CH=CHCH_3$ | 2.7 | 1.0 | 3.0 | .2 | 3.1 | trace |
| 2 = cisoid $CH_3OC(O)CH=CHCH=CH_2$ | trace | trace | trace | trace | trace | trace |
| 3 = transoid $CH_3OC(O)CH=CHCH=CH_2$ | 20.1 | 17.3 | 16.7 | 13.1 | 9.6 | 22.2 |
| 4 = $CH_3OC(O)CH_2CH(OCH_3)CH=CH_2$ | .5 | .7 | 1.6 | 1.4 | .7 | .7 |
| 6 = cis $CH_3OCH_2CH=CHCH_2CO_2CH_3$ | trace | trace | trace | trace | trace | trace |
| 7 = trans $CH_3OCH_2CH=CHCH_2CO_2CH_3$ | 4.1 | 3.5 | 3.3 | 2.9 | 4.1 | 2.3 |
| 12 = cis $CH_3O_2CCH_2CH=CHCH_2CO_2CH_3$ | 13.6 | 14.7 | 14.2 | 15.4 | 15.9 | 16.1 |
| 13 = trans $CH_3O_2CCH_2CH=CHCH_2CO_2CH_3$ | 56.2 | 60.1 | 58.3 | 65.0 | 64.1 | 55.7 |
| 14 = $CH_3OC(O)CH=CHCH=CHCO_2CH_3$ | 2.7 | 2.7 | 2.9 | 2.0 | 2.6 | 3.7 |
| Total 12, 13 and 14 | 72.5 | 77.5 | 75.4 | 82.4 | 82.6 | 75.5 |
| Selectivity (mole %, on CO) | | | | | | |
| 1 = $CH_3O_2CCH_2CH=CHCH_3$ | 1.1 | .4 | 1.3 | .1 | 1.5 | trace |
| 3 = transoid $CH_3OC(O)CH=CHCH=CH_2$ | 8.1 | 7.0 | 7.0 | 6.5 | 4.6 | 11.6 |
| 5 = $CH_3O(O)CC(O)OCH_3$ | 1.4 | 2.3 | 2.0 | .7 | 1.0 | 1.7 |
| $CO_2$ | 29.2 | 25.9 | 24.6 | 8.3 | 10.7 | 7.3 |

TABLE 5-continued

| | | | | | | |
|---|---|---|---|---|---|---|
| Total 12, 13 and 14 | 58.4 | 62.7 | 63.1 | 82.3 | 79.9 | 78.1 |

| Example No. | 33 | 34 | 35 | 36 | 37 | 38 |
|---|---|---|---|---|---|---|
| Recycle Number | 3rd Pass | 4th Pass | 1st Pass | 2nd Pass | 3rd Pass | 4th Pass |
| Reaction Conditions | | | | | | |
| HCL (mmole) | 8.0 | 8.0 | — | 4.0 | 4.0 | 4.0 |
| HCL (mole/liter) | .05 | .05 | — | .027 | 0.27 | .027 |
| $VCl_3$ (mmole) | — | — | 5.0 | — | — | — |
| % Conversion | 32.5 | 32.9 | 32.7 | 36.3 | 30.8 | 28.9 |
| DMOC Balance (%) | 91.0 | 98.5 | 89.5 | 98.1 | 98.8 | 96.3 |
| BD Balance (%) | 88.2 | 90.8 | 86.2 | 85.2 | 84.9 | 91.0 |
| % of Original Activity | 92.6 | 93.7 | — | 111.0 | 94.2 | 88.4 |
| Selectivity (mole %, on BD) | | | | | | |
| 1 = $CH_3O_2CCH_2CH=CHCH_3$ | trace | trace | 2.3 | .2 | trace | trace |
| 2 = cisoid $CH_3OC(O)CH=CHCH=CH_2$ | trace | trace | trace | trace | trace | trace |
| 3 = transoid $CH_3OC(O)CH=CHCH=CH_2$ | 25.4 | 24.4 | 10.2 | 25.1 | 31.6 | 31.6 |
| 4 = $CH_3OC(O)CH_2CH(OCH_3)CH=CH_2$ | .8 | 1.2 | .7 | .6 | .7 | .6 |
| 6 = cis $CH_3OCH_2CH=CHCH_2CO_2CH_3$ | trace | trace | trace | trace | trace | trace |
| 7 = trans $CH_3OCH_2CH=CHCH_2CO_2CH_3$ | 1.5 | 2.3 | 3.2 | 1.1 | .8 | 1.0 |
| 12 = cis $CH_3O_2CCH_2CH=CHCH_2CO_2CH_3$ | 13.2 | 12.0 | 16.2 | 13.2 | 11.4 | 16.8 |
| 13 = trans $CH_3O_2CCH_2CH=CHCH_2CO_2CH_3$ | 55.0 | 52.9 | 65.3 | 55.9 | 51.8 | 72.5 |
| 14 = $CH_3OC(O)CH=CHCH=CHCO_2CH_3$ | 4.1 | 6.7 | 2.1 | 3.8 | 3.7 | 7.4 |
| Total 12, 13 and 14 | 72.3 | 71.6 | 83.5 | 72.9 | 66.9 | 76.7 |
| Selectivity (mole %, on CO) | | | | | | |
| 1 = $CH_3O_2CCH_2CH=CHCH_3$ | trace | trace | 1.1 | .1 | trace | trace |
| 3 = transoid $CH_3OC(O)CH=CHCH=CH_2$ | 13.6 | 13.3 | 4.9 | 13.4 | 17.8 | 17.6 |
| 5 = $CH_3O(O)CC(O)OCH_3$ | 2.3 | 1.4 | .6 | 2.0 | 1.6 | 3.3 |
| $CO_2$ | 5.2 | 4.2 | 11.9 | 6.2 | 4.7 | 3.8 |
| Total 12, 13 and 14 | 77.7 | 80.0 | 79.6 | 77.5 | 75.1 | 74.6 |

EXAMPLES 39–49

All reactants were charged into a 300 ml "Magnedrive" Hastelloy "C" autoclave. Reaction conditions included a reaction temperature of 100° C. at 1800 psi total system pressure. In all experiments, 1,3-butadiene (50 ml-500 mmole) was allowed to come to thermal equilibrium before it was charged into the autoclave as a liquid via the use of a sight glass. Carbon monoxide (1100 psi) was charged to the autoclave followed by heating to 100° C. After thermal equilibrium was obtained, the carbon monoxide pressure was adjusted to 1600 psi. Oxygen and carbon monoxide were charged in increments of 100 psi $O_2$ and 100 psi CO and subsequent 50 psi $O_2$ and 100 psi CO additions were made at intervals so that the gases were never potentially explosive. 72.00 g (500 mmoles) 1,1-dimethoxychlorohexane was used as a dehydration agent in each of the reactions along with 2.5 g (78 mmole) of methanol. The autoclave residence time for all of Examples 39–49 was 120 minutes and the oxygen addition frequency was 20 minutes. The stirring rate was 1000 rpm. The catalyst system comprised $PdCl_2$ (2.5 mmole), $CuCl_2$ (12.5 mmole), LiCl (5.0 mmole) and $VCl_3$ (5.0 mmole). Product selectivities expressed in mol percent based on 1,3-butadiene are based on the mmoles of 1,3-butadiene required to make each product. The amount of unreacted 1,3-butadiene was obtained by mass spectral analysis of the autoclave gases and glc analysis for butadiene in the liquid product. Product selectivities expressed in mol percent based on CO are based on the mmoles of carbon monoxide required to make each product. Only the more important product selectivities are calculated and shown. Table 6 sets forth the results of Examples 39–49 which serve to illustrate the effect of the addition of small quantities of anhydrous hydrochloric acid to the catalyst system. Experiments 27–49 show that the use of 0.05 to 0.10 moles/liter of anhydrous hydrochloric acid is favored.

TABLE 6

| Example No. | 39 | 40 | 41 | 42 | 43 | 44 |
|---|---|---|---|---|---|---|
| Recycle No. | 1st Pass | 2nd Pass | 3rd Pass | 4th Pass | 1st Pass | 2nd Pass |
| Reaction Conditions | | | | | | |
| HCl (mmole) | — | 12.0 | 12.0 | 12.0 | — | 8.0 |
| HCl (mole/liter) | — | .075 | .075 | .075 | — | .05 |
| $VCl_3$ (mmole) | 5.0 | — | — | — | — | — |
| % Conversion | 32.4 | 32.0 | 32.3 | 28.8 | 44.2 | 34.0 |
| DMOC Balance (%) | 86.7 | 92.0 | 97.2 | 92.7 | 106 | 92.0 |
| BD Balance (%) | 85.3 | 87.2 | 95.0 | 86.5 | 90.2 | 85.3 |
| % of Original Activity | — | 98.8 | 99.7 | 88.9 | — | 76.8 |
| Selectivity (mole %, on BD) | | | | | | |
| 1 = $CH_3O_2CCH_2CH=CHCH_3$ | 1.9 | trace | 2.0 | trace | 1.9 | trace |
| 2 = cisoid $CH_3OC(O)CH=CHCH=CH_2$ | trace | trace | trace | trace | trace | trace |
| 3 = transoid $CH_3OC(O)CH=CHCH=CH_2$ | 12.8 | 18.6 | 12.3 | 16.9 | 17.3 | 15.8 |
| 4 = $CH_3OC(O)CH_2CH(OCH_3)CH=CH_2$ | .7 | .8 | .8 | .8 | .5 | .8 |
| 6 = cis $CH_3OCH_2CH=CHCH_2CO_2CH_3$ | trace | trace | trace | trace | trace | trace |
| 7 = trans $CH_3OCH_2CH=CHCH_2CH_3$ | 3.6 | 2.9 | 1.4 | 2.3 | 3.6 | 1.3 |
| 12 = cis $CH_3O_2CCH_2CH=CHCH_2CO_2CH_3$ | 15.0 | 14.1 | 14.8 | 15.0 | 14.6 | 15.1 |
| 13 = trans $CH_3O_2CCH_2CH=CHCH_2CO_2CH_3$ | 62.4 | 60.6 | 66.1 | 63.4 | 58.2 | 63.7 |
| 14 = $CH_3OC(O)CH=CHCH=CHCO_2CH_3$ | 3.6 | 3.2 | 2.7 | 1.7 | 3.8 | 3.4 |
| Total 12, 13 and 14 | 81.0 | 77.9 | 83.6 | 80.1 | 76.6 | 82.2 |
| Selectivity (mol %, on CO) | | | | | | |

TABLE 6-continued

| | | | | | | |
|---|---|---|---|---|---|---|
| 1 = $CH_3O_2CCH_2CH=CHCH_3$ | .9 | trace | 1.0 | trace | 1.0 | trace |
| 3 = transoid $CH_3OC(O)CH=CHCH=CH_2$ | 6.9 | 8.4 | 6.3 | 8.8 | 9.0 | 7.8 |
| 5 = $CH_3O(O)CC(O)OCH_3$ | 1.5 | 2.6 | 1.0 | .8 | 2.2 | 2.0 |
| $CO_2$ | 13.9 | 16.9 | 4.4 | 5.1 | 5.4 | 8.7 |
| Total 12, 13 and 14 | 75.6 | 70.8 | 86.2 | 83.6 | 80.2 | 80.5 |

| Example No. | 45 | 46 | 47 | 48 | 45 |
|---|---|---|---|---|---|
| Recycle No. | 3rd Pass | 4th Pass | 5th Pass | 6th Pass | 7th Pass |
| Reaction Conditions | | | | | |
| HCl (mmole) | 8.0 | 8.0 | 8.0 | 8.0 | 8.0 |
| HCl (mole/liter) | .05 | .05 | .05 | .05 | .05 |
| $VCl_3$ (mmole) | — | — | — | — | — |
| % Conversion | 33.2 | 34.2 | 30.4 | 35.3 | 25.2 |
| DMOC Balance (%) | 101 | 100.5 | 99.0 | 98.8 | 97.7 |
| BD Balance (%) | 93.8 | 93.5 | 87.1 | 95.6 | 95.5 |
| % of Original Activity | 75.1 | 77.4 | 68.8 | 79.9 | 57.0 |
| Selectivity (mole %, on BD) | | | | | |
| 1 = $CH_3O_2CCH_2CH=CHCH_3$ | trace | .4 | trace | trace | trace |
| 2 = cisoid $CH_3OC(O)CH=CHCH=CH_2$ | trace | trace | trace | trace | trace |
| 3 = transoid $CH_3OC(O)CH=CHCH=CH_2$ | 28.2 | 23.7 | 27.2 | 16.5 | 33.9 |
| 4 = $CH_3OC(O)CH_2CH(OCH_3)CH=CH_2$ | .8 | .7 | .8 | .7 | 1.0 |
| 6 = cis $CH_3OCH_2CH=CHCH_2CO_2CH_3$ | trace | trace | trace | trace | trace |
| 7 = trans $CH_3OCH_2CH=CHCH_2CO_2CH_3$ | 1.1 | 1.6 | 2.0 | 1.4 | 1.4 |
| 12 = cis $CH_3O_2CCCH_2CH=CHCH_2CO_2CH_3$ | 12.3 | 13.2 | 13.8 | 14.9 | 11.7 |
| 13 = trans $CH_3O_2CCCH_2CH=CHCH_2CO_2CH_3$ | 52.7 | 56.2 | 54.5 | 63.5 | 48.8 |
| 14 = $CH_3OC(O)CH=CHCH=CHCO_2CH_3$ | 4.8 | 4.2 | 1.7 | 3.0 | 3.3 |
| Total 12, 13 and 14 | 69.8 | 73.6 | 70.0 | 81.4 | 63.8 |
| Selectivity (mole %, on CO) | | | | | |
| 1 = $CH_3O_2CCH_2CH=CHCH_3$ | trace | .2 | trace | trace | trace |
| 3 = transoid $CH_3OC(O)CH=CHCH=CH_2$ | 15.5 | 12.9 | 15.2 | 8.8 | 19.2 |
| 5 = $CH_3O(O)CC(O)OCH_3$ | 1.9 | 2.3 | 2.1 | 1.8 | 2.2 |
| $CO_2$ | 5.0 | 2.8 | 3.3 | 1.7 | 5.3 |
| Total 12, 13 and 14 | 76.6 | 80.4 | 78.2 | 86.7 | 72.1 |

I claim:

1. In the process for preparing an unsaturated diester having the formula

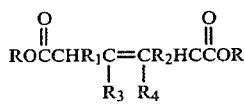

wherein R is alkyl having 1 to 8 carbon atoms or aralkyl having 6 carbon atoms in the ring and 1 to 4 carbon atoms in the alkyl moiety and $R_1$, $R_2$, $R_3$ and $R_4$ are the same or different and are each hydrogen, halogen, alkyl having 1 to 4 carbon atoms or aryl having 6 carbon atoms in the ring by reacting a diolefin having the formula

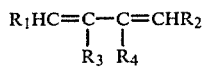

wherein $R_1$, $R_2$, $R_3$, and $R_4$ are as aforesaid, with a mixture of carbon monoxide and oxygen and a stoichiometric amount of a dehydrating agent selected from the group consisting of acetals, ketals, carboxylic ortho esters, trialkylorthoborates and dialkoxycycloalkanes, at a pressure of from about 15 psig to 5,000 psig and at a temperature of about 25° to 200° C. in the presence of an effective amount of a catalytic mixture of (1) a platinum group metal compound or mixtures thereof and (2) a copper (I), copper (II), iron (II) or iron (III) oxidant salt compound and recovering the desired unsaturated diester, the improvement comprising carrying out said reaction in the presence of from 0.3 to 3 weight percent of a vanadium salt which is soluble in the reaction mixture under reaction conditions.

2. The process of claim 1 wherein said reaction is also carried out in the presence of an anhydrous halogen-containing acid selected from the group consisting of hydrochloric, hydrobromic and hydroiodic acid at a concentration of from 0.01 to 1 mole/liter.

3. The process of claim 2 wherein said acid is hydrochloric acid.

4. The process of claim 3 wherein said hydrochloric acid is generated in situ by the thermal disassociation of 1-chloro-1-methoxycyclohexane.

5. The process of claim 1 wherein said soluble vanadium salt is a chloride, bromide or iodide of vanadium (III).

6. The process of claim 1 wherein the reaction is carried out in the presence of a catalytic amount of a monohydric saturated aliphatic, alicyclic or aralkyl alcohol containing from 1 to 20 carbon atoms which may contain other substituents which would not interfere with the reaction.

7. The process of claim 1 wherein the reaction is carried out in the presence of an organic mono- or polydentate ligand or coordination complex compound selected from the group consisting of alkyl, aryl, and halogen substituted phosphines, arsines, stibines, and alkali metal salts.

8. In the process of preparing dimethylhex-3-endioate by reacting 1,3-butadiene with a mixture of carbon monoxide and oxygen and a stoichiometric quantity of a dehydrating agent selected from the group consisting of acetals, ketals, carboxylic ortho esters, trialkylorthoborates and dialkoxycycloalkanes, at a pressure of between about 500 psig and 1800 psig and at a temperature of from about 80° to 150° C. in the presence of an effective amount of a palladium metal salt compound and a copper (II) oxidant salt compound, the improvement comprising carrying out said reaction in the presence of from 0.3 to 3 weight percent of a soluble vanadium salt.

9. The process of claim 8 wherein said reaction is also carried out in the presence of an anhydrous halogen-containing acid selected from the group consisting of hydrochloric, hydrobromic and hydroiodic acid at a concentration of from 0.01 to 1 mole/liter.

10. The process of claim 1 wherein said dehydrating agent is 1,1-dimethoxycyclohexane.

* * * * *